United States Patent [19]

Philippe et al.

[11] Patent Number: 5,230,890
[45] Date of Patent: Jul. 27, 1993

[54] URETHANE DERIVATIVES FROM AMINO ACIDS, A PROCESS FOR THEIR PREPARATION AND COSMETIC OR PHARMACEUTICAL COMPOSITIONS FOR USE IN THE TREATMENT OF DRY SKIN

[75] Inventors: Michel Philippe, Antony; Henri Sebag, Paris; Guy Vanlerberghe, Montjay La Tour; Jean De Rigal, Claye Souilly, all of France

[73] Assignee: L'Oreal, Paris, France

[21] Appl. No.: 550,740

[22] Filed: Jul. 10, 1990

[30] Foreign Application Priority Data

Jul. 11, 1989 [FR] France .................. 89 09328

[51] Int. Cl.$^5$ .................. A61K 7/48; A61K 7/50; A61K 7/075; C07C 229/116
[52] U.S. Cl. .................. 424/401; 424/70; 424/DIG. 5; 424/443; 424/484; 514/563; 514/846; 514/847; 514/873; 514/975; 562/561; 562/564; 562/567
[58] Field of Search .................. 560/160, 167; 514/563, 514/613, 616, 747; 424/401; 562/567; 252/351, 356, 357

[56] References Cited

U.S. PATENT DOCUMENTS

| | | | |
|---|---|---|---|
| 3,532,736 | 10/1970 | Chamberlin | 560/160 |
| 3,758,525 | 9/1973 | Yoshida et al. | 260/404 |
| 3,775,466 | 2/1973 | Jager et al. | 260/482 |
| 3,920,730 | 10/1975 | Gleason | 560/160 |
| 3,948,971 | 4/1976 | Veber et al. | 530/337 |
| 3,953,608 | 4/1970 | Vanlerberghe | 514/777 |
| 4,089,954 | 5/1978 | Morelle | 514/563 |
| 4,112,085 | 9/1978 | Morelle | 514/563 |
| 4,304,933 | 12/1981 | Mita | 562/567 |
| 4,436,726 | 3/1984 | Umehara et al. | 514/19 |
| 4,661,606 | 4/1987 | Tuominen et al. | 548/496 |
| 4,732,892 | 3/1988 | Sarpotdar et al. | 514/178 |
| 4,743,442 | 5/1988 | Raaf | 514/847 |
| 4,822,890 | 4/1989 | Bolin | 548/344 |
| 4,873,087 | 10/1989 | Morishita et al. | 424/433 |

FOREIGN PATENT DOCUMENTS

638521 10/1963 Belgium .
2192795 2/1974 France .
2140297 11/1984 United Kingdom .

OTHER PUBLICATIONS

Biochemical and Organic Compounds for Research and Diagnostic Clinical Reagents, Feb. 1985, p. 287, Sigma Chemie GmbH, Products C5252, C1760.
Chemical Abstracts, vol. 65, 1966, Nr. 10657, Poroshin et al: "Effect of substituents in carbocyclohexyloxy group on the rate of its cleavage in hydrobrominolysis".
Journal of the American Medical Society, vol. 79, 1957, pp. 4686-4690, McKay et al: "New amine-masking for peptide synthesis".
T. W. Greene: "Protective groups in organic synthesis", Aug. 1981, pp. 222-248.
French Search Report of FR 89 09328.

*Primary Examiner*—Thurman K. Page
*Assistant Examiner*—Edward J. Webman
*Attorney, Agent, or Firm*—Cushman, Darby & Cushman

[57] ABSTRACT

A urethane derivative from amino acids has the formula $$R'O-CO-NH-CH(R)-COOH \quad (I)$$

wherein R represents $-CH_2OH$, $-CHOH-CH_3$ or $-(CH_2)_3-NH-CO-NHY$, Y represents $-H$ or $-COOR'$, R' represents linear or branched alkyl, optionally unsaturated, having 8-24 carbon atoms, or a monocyclic cycloalkyl substituted by an alkyl whose total number of carbon atoms is equal to or greater than 10, or to the salts of the derivative of formula I or to a mixture of the derivatives of formula I and/or their salts. A method is given for the preparation of the urethane derivative of formula I, as are examples of cosmetic or pharmaceutical compositions containing the urethane derivative, as a hydrating agent, for the treatment of dry skin.

3 Claims, 1 Drawing Sheet

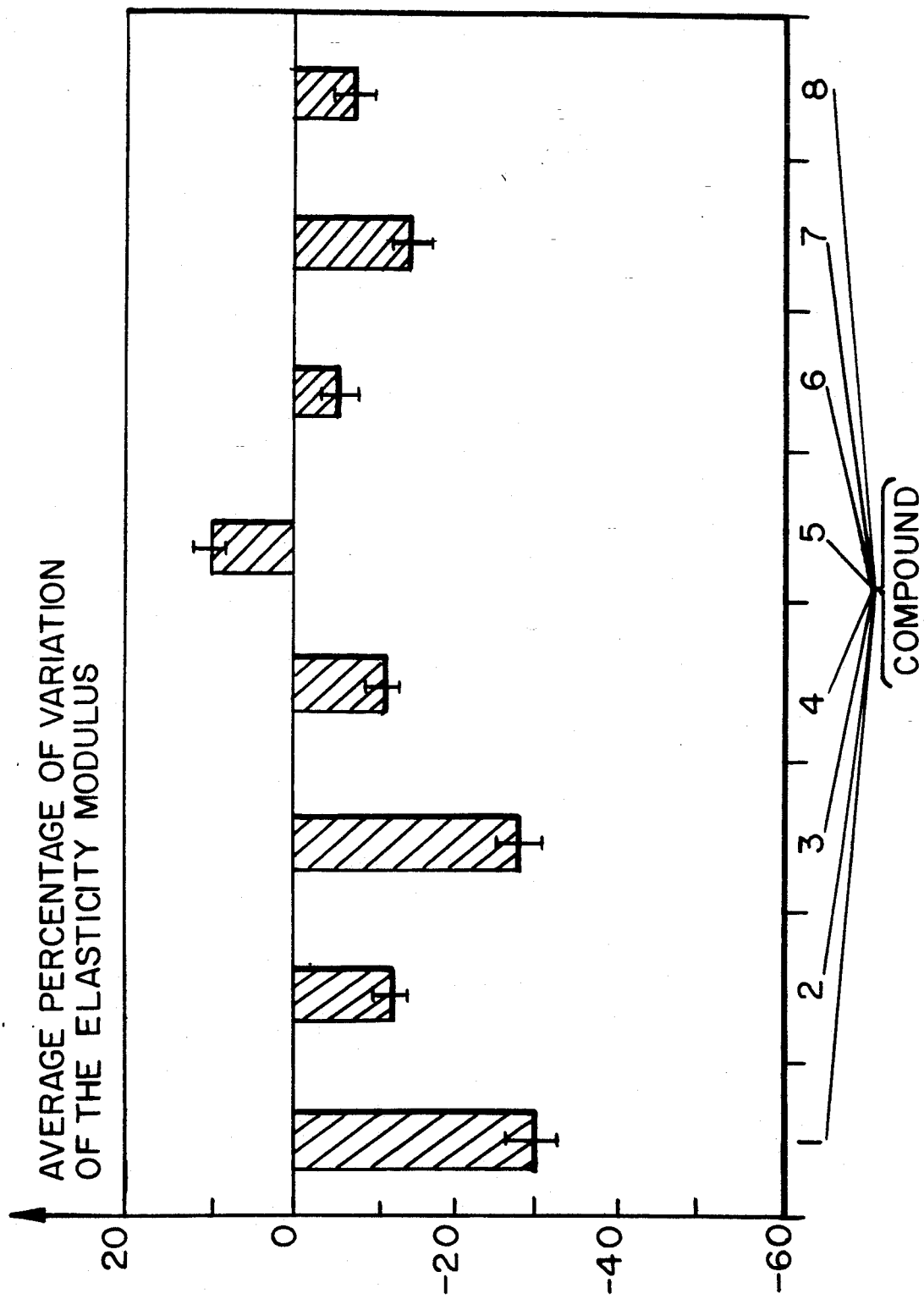

URETHANE DERIVATIVES FROM AMINO ACIDS, A PROCESS FOR THEIR PREPARATION AND COSMETIC OR PHARMACEUTICAL COMPOSITIONS FOR USE IN THE TREATMENT OF DRY SKIN

The present invention relates to new urethanes derived from amino acids, to their preparation and to their use, principally as hydrating agents or as mild surfactants in cosmetic or pharmaceutical compositions.

BRIEF DESCRIPTION OF THE DRAWING

FIG. 1 shows the improvement in elasticity of delipidated stratum corneum upon application of the invention in comparison to closely related compounds.

The present invention more precisely relates to urethane derivatives having the formula

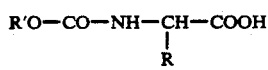

(I)

wherein

R represents —CH$_2$OH, —CHOH—CH$_3$ or —(CH$_2$)$_3$—NH—CO—NHY, wherein Y represents —H or —CO—OR', R' represents linear or branched alkyl, optionally unsaturated, having 8-24 carbon atoms, or a monocyclic cycloalkyl substituted by an alkyl, the total number of carbon atoms of which is equal to or greater than 10, as well as the salts of the compounds of formula I and mixtures of the compounds of formula I and/or their salts.

Representative salts of the compounds of formula I, include those salts which are compatible with application the skin, and principally metallic salts, such as a sodium salt, a zinc salt, a magnesium salt, an aluminum salt and a cupric salt or salts of organic cations such as a quaternary ammonium salt of the formula

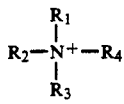

wherein R$_1$, R$_2$, R$_3$ and R$_4$, each independently, represent —CH$_3$, —CH$_2$—C$_6$H$_5$ or —CH$_2$—CH$_2$OH.

In the compounds of formula I, R' represents, principally, an alkyl group having preferably 8 to 24 carbon atoms, or a mono- or poly-unsaturated alkyl such as, for example, a C$_{18}$ mono-unsaturated alkyl, a cycloalkyl having, for example, 5 or 6 chains substituted by an alkyl, the total number of carbon atoms being equal to or greater than 10, such as (t-butyl) cyclohexyl.

The present invention also relates to a process for preparing the compounds of formula I.

This process comprises reacting a salt of an amino acid (D-, L- or DL) selected from serine, threonine and citrulline with a compound of formula II having the formula

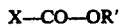

(II)

wherein

X represents halogen or a 1-imidazolyl group, in an appropriate solvent, isolating, in accordance with known methods, the corresponding formed urethane derivative of formula I and that, if desired, transforming, in accordance with known methods, the said urethane derivative into the corresponding salt.

The starting salt is, for example, a salt of an alkaline metal or an amine salt such as triethylamine.

The reaction between the salt of an acid amino and halogenoformate (preferably, the chloroformate) can be carried out at ambient temperature in a classic solvent such as a water-tetrahydrofuran, water-dioxan or water-pyridine mixture. The reaction between the salt of the amino acid and the derivative of imidazole of formula II can be carried out, for example, in N,N-dimethylformamide or N,N-dimethylacetamide at a temperature of 20° to 100° C., for example, at 60° C., in the presence of a basic catalyst such as potassium t-butanolate or sodium imidazolidide.

It can be seen, according to formula I, that the mentioned process permits the creation of a urethane function of which nitrogen proceeds from the amine function of the amino acid. In the case of citrulline, a urein function can also be created (see the definition of Y) by reaction of the compound of formula II with the ureido function of the citrulline. This latter reaction certainly takes place only in the presence of a sufficient amount of the compound of formula II.

The compounds of formula I and their salts can be employed in man as hydrating agents for the skin, and they permit to conserve or restore the suppleness of the skin, its elasticity, its resistance to movements of the body and its barrier function to the entrance of toxic substances. It is known that cosmetic or dermopharmaceutical compositions intended to hydrate the skin (hydrating preparations) are employed with persons having so-called dry skin. This phenomenon is generally characterized by a skin having an evaporation rate clearly higher than that of healthy skin, by a loss of cutaneous elasticity and by the formation of wrinkles. It can be caused principally by pathological disorders of keratinization, by ageing or by excessive exposure to the sun or by various external agents (detergents, soaps, solvents, dry atmosphere, etc.). The phenomenon can affect all parts of the body and particularly the face, neck and hands.

The urethane derivatives of the present invention also have surface-active properties and can be employed as mild detergents in cosmetic or pharmaceutical compositions for the skin and hair.

Besides, certain urethane derivatives of the present invention can form in water or in aqueous solvents vesicular structures capable of trapping and retaining hydrophobic or hydrophilic substances, and can be employed as vehicles for lipophilic or hydrophilic active ingredients, principally in cosmetic o pharmaceutical compositions.

The present invention also relates to a cosmetic or pharmaceutical composition characterized by the fact that it comprises, as an active ingredient, at least one urethane derivative, such as defined above, in a vehicle compatible with application to the skin and/or on the hair.

In the compositions of the present invention, the urethane derivative is present in an amount ranging from 0.1 to 15 weight percent, and preferably from 0.5 to 5 weight percent, based on the total weight of the composition.

The compositions of the present invention are principally lotion-type solutions or emulsions, foaming or not; milk-type emulsions having a liquid or semi-liquid consistency, obtained by dispersing a fatty or oily phase in an aqueous phase, or vice versa; cream-type suspensions or emulsions having a soft consistency; or solid preparations such as sticks or cleansing cakes.

The vehicles present in the compositions of the invention are conventional vehicles employed in this class of composition. It is a question, for example, of water and organic solvents compatible with cutaneous application such as, for example, acetone, isopropyl alcohol, ethyl alcohol, $C_6$–$C_{24}$ fatty acid triglycerides, glycol ethers such as the lower alkyl ethers of mono- or di-alkylene glycol, the alkylene moiety having, for example, 2–4 carbon atoms. There can also be employed, as the solvent, esters of polyalkylene glycol and $C_1$–$C_4$ short chain acids, or even volatile silicones.

The compositions can also contain, if necessary, fatty bodies, principally oils, natural or synthetic.

The compositions of the present invention can also include thickening or gelling agents such as cellulose or cellulose derivatives, for example, in the amount of 0.5 to 20 weight percent with respect to the total weight of the composition. The thickening agents can also be constituted by acrylic polymers, alginates, gums such as xanthan gum, guar, carbo, gum arabic or even polyethylene glycols, bentontes and montmorillonites.

The compositions of the present invention can also contain other known hydrating agents or humectants, such as glycerine, triacetin, or more generally other active ingredients such as agents which are active in combatting skin ageing.

The compositions of the present invention can also contain conventional adjuvants such as antioxidants, preservatives, perfumes, dyes and the like.

Representative anti-oxidants include tert. butylhydroxyquinone, butylhydroxyanisole, butylhydroxytoluene and α-tocopherol and its derivatives.

The compositions of the present invention are provided principally in the form of creams, milks, gels, lotions which optionally can be thickened, foaming solutions for the douche or bath, impregnated pads, salves, sticks or in the form of cakes or hydrating masks.

The compositions for the hair are principally shampoos in which the urethane derivative can be combined with other surfactants such as anionic, cationic, nonionic or amphoteric surfactants or mixtures thereof.

The compositions of the present invention can also be provided in the form of solutions or emulsions containing the urethane derivative, such as defined above, in vesicular form, the vesicles being able to serve as encapsulation agents, lipophilic or hydrophilic active ingredients such as retinoic acid, ultraviolet filtering agents and principally other hydrating agents All these compositions are prepared in accordance with conventional procedures.

The present invention also has for an object the use of a urethane derivative, such as defined above, as an active ingredient in the preparation of a cosmetic or pharmaceutical composition intended for the treatment or care of dry skin.

The present invention also relates to a cosmetic treatment intended principally to improve the appearance and elasticity of the skin of persons having dry skin, or intended to prevent the appearance of esthetic disorders caused by this dry skin phenomenon, characterized by the fact that a cosmetic composition, such as defined above, is applied to the skin of the portions of the body concerned, including optionally the scalp.

The application of the composition of the present invention is carried out in accordance with conventional procedures.

The cosmetic treatment process of the present invention is applicable principally in the case of dry dermatosis, ichthyosis, xeroses and the like.

The following non-limiting examples illustrate the invention.

EXAMPLE 1

Preparation of N-hexadecyloxycarbonyl (D,L)-serine 15 g of (D,L)-serine are dissolved in 50 ml of water at ambient temperature. 143 meq of sodium hydroxide in the form of a 10 meq/g aqueous solution are added and the mixture is stirred for 20 minutes. 50 ml of tetrahydrofuran are added with vigorous stirring. There are then slowly added (over a period of 1 hour) 48.7 g of cetyl chloroformate while maintaining the pH of the medium at a value greater than 9, which requires the further addition of 143 meq of sodium hydroxide in the form of a 10 meq/g aqueous solution. The medium is left, under vigorous agitation, for 1 hour while continuing to maintain a pH greater than 9. 250 ml of a 10% aqueous solutions of HCl are added and the urethane formed is extracted with ethyl acetate (250 ml). The organic phase is dried on sodium sulfate, the solvents are evaporated under a vacuum and the resulting dry residue is crystallized in heptane. 32 g (60% yield) of N-hexadecyloxy carboxyl (D,L)-serine in the form of a white powder are obtained.

The product, recrystallized in an isopropyl ether/heptane mixture, melts at 89° C.

Elemental analysis: $C_{20}H_{39}NO_5.0.5H_2O$; M.W.=382.5

|  | C | H | N |
|---|---|---|---|
| Calculated, % | 62.8 | 10.54 | 3.66 |
| Found, % | 63.22 | 10.55 | 3.67 |

The NMR $^{13}$C (CDCl$_3$/CD$_3$OD-T.M.S.) spectrum conforms to the indicated structure with a displacement of the urethane carbonyl at 157.31 p.p.m. and a displacement of the acid carbonyl at 172.98 p.p.m.

In an analogous fashion the corresponding derivatives of threonine and citrulline are prepared.

EXAMPLE 2

Preparation of N-(2-ethylhexyloxycarbonyl) (D,L)-serine 42 g of (D,L)-serine are dissolved in 100 ml of water. Then 400 meq. of NaOH using a 10 meq/g aqueous solution (40 g) are added. The medium is stirred for 20 minutes, and 100 ml of tetrahydrofuran are added while increasing the stirring. There are slowly added, over a 1 hour period, 77.4 g of 2-ethylhexyl chloroformate while maintaining the pH of the medium at a value greater than 9, which requires again adding, during the course of this addition, 400 meq. of soda in the form of a 10 meq/g solution. The medium is left, under vigorous stirring, for 1 hour while continuing to maintain the pH greater than 9. 500 ml of a 10% aqueous HCl solution are added and the formed urethane is extracted with ethyl acetate (500 ml). The organic phase is dried on sodium sulfate, the solvents are evaporated under a vacuum and the resulting viscous liquid is crystallized in heptane to provide 60 g (60% yield) of N-2-ethylhexyloxycarbonyl (D,L)-serine in the form of a white powder.

The resulting product, recrystallized in an isopropyl ether/heptane mixture melts at 37° C.

Elemental analysis: $C_{12}H_{23}NO_5.0.5H_2O$; M.W. = 270.3

|  | C | H | N |
|---|---|---|---|
| Calculated, % | 53.32 | 8.95 | 5.18 |
| Found, % | 52.98 | 8.93 | 5.04 |

The NMR $^{13}C$ (CDCl$_3$/CD$_3$OD-T.M.S.) spectrum conforms to the indicated structure with a displacement of the urethane carbonyl at 157.42 p.p.m. and a displacement of the acid carbonyl at 172.96 p.p.m.

In an analogous manner the corresponding derivatives of threonine and citrulline are prepared.

EXAMPLE 3

Preparation of the triethanolamine salt of N-hexadecyloxycarbonyl (D,L)-serine

A mixture of 223.8 g of N-hexadecyloxycarbonyl (D,L)-serine and 89.4 g of triethanolamine in 400 ml of isopropanol is heated at 65° C. for 1 hour. The solvent is then evaporated under a vacuum to obtain 313 g of the expected salt in crystalline form. Melting point = 73°-75° C.

Elemental analysis: $C_{26}H_{54}N_2O_8$; M.W. = 522.7

|  | C | H | N |
|---|---|---|---|
| Calculated, % | 59.74 | 10.41 | 5.36 |
| Found, % | 59.26 | 10.31 | 5.37 |

The NMR $^{13}C$ (CD$_3$OD-T.M.S.) spectrum conforms to expected structure.

In an analogous manner the corresponding threonine and citrulline derivatives are prepared.

EXAMPLE 4

Preparation of the triethanolamine salt of N-(2-ethylhexyloxycarbonyl) (D,L)-serine This salt is obtained in a manner analogous to that described in Example 3. It is obtained in the form of an amber wax.

Elemental analysis: $C_{18}H_{38}N_2O_8.0.5$ $H_2O$; M.W. = 419.7

|  | C | H | N |
|---|---|---|---|
| Calculated, % | 51.51 | 9.36 | 6.70 |
| Found, % | 51.69 | 9.36 | 6.73 |

The NMR $^{13}C$ (CD$_3$OD-T.M.S.) spectrum conforms to expected structure.

In an analogous fashion the corresponding threonine and citrulline derivatives are prepared.

EXAMPLE 5

Preparation of N-dodecyloxycarbonyl (D,L)-serine

The method of operation is analogous to that described in Example 1.

The resulting product, recrystallized in heptane, melts at 92° C.

Elemental analysis: $C_{16}H_{31}NO_5.0.5$ $H_2O$; M.W. = 326

|  | C | H | N |
|---|---|---|---|
| Calculated, % | 58.87 | 9.88 | 4.29 |
| Found, % | 58.15 | 9.97 | 3.84 |

The NMR $^{13}C$ (CDCl$_3$4/CD$_3$OD 1 - T.M.S.) spectrum conforms to the indicated structure with a displacement of the urethane carbonyl at 157.36 p.p.m. and a displacement of the acid carbonyl at 173.05 p.p.m.

EXAMPLE 6

Preparation of N-p.tert.butylcyclohexyloxycarbonyl (D,L)-serine

The method of operation is analogous to that of Example 1.

The product, recrystallized in a water/heptane mixture, melts at 79° C.

Elemental analysis: $C_{17}H_{31}N_3O_5.0.5$ $H_2O$; M.W. = 366.5

|  | C | H | N |
|---|---|---|---|
| Calculated, % | 55.72 | 8.81 | 11.47 |
| Found, % | 56.06 | 8.71 | 11.53 |

The NMR $^{13}C$ (CD$_3$OD - T.M.S.) spectrum conforms to the indicated structure with a displacement of the urethane carbonyl at 158.5 p.p.m. and a displacement of the ureido carbonyl at 162.2 p.p.m. and a displacement of the acid carbonyl at 175.9 p.p.m.

EXAMPLE 7

Preparation of the sodium salt of N-hexadecyloxycarbonyl (D,L)-serine

This product is obtained by the neutralization of the product of Example 1 by soda in an isopropanol/water mixture at 60° C. Melting point = 155° C. (isopropanol/water).

Elemental analysis: $C_{20}H_{38}NO_5Na$; M.W. = 395.5

|  | C | H | N | O |
|---|---|---|---|---|
| Calculated, % | 60.73 | 9.63 | 3.54 | 20.23 |
| Found, % | 60.87 | 9.65 | 3.43 | 20.76 |

EXAMPLE 8

Preparation of the sodium salt of N-2-ethylhexyloxycarbonyl (D,L)-serine

This product is obtained by the neutralization of the product Example 2 by soda in an isopropanol/water mixture at 20° C. Melting point = 85° C. (isopropanol/water).

Elemental analysis: $C_{12}H_{22}NO_5Na$; M.W. = 283.3

|  | C | H | N | O |
|---|---|---|---|---|
| Calculated, % | 50.87 | 7.83 | 4.94 | 28.24 |
| Found, % | 50.91 | 7.68 | 4.76 | 28.41 |

Comparative study of the influence of the urethane derivatives of the present invention on the elasticity of a delipidated stratum corneum This study is carried out using the device to determine the elasticity of skin, described by L. Rasseneur, J. De Rigal and J. L. Leveque, Int. J. of Cosm. Sci. 4, 247–260 (1982).

The elasticity of a previously delipidated stratum corneum on which there has been applied 3% solutions of the product being studied in a 2:1 chloroform/methanol mixture is measured. Previously delipidating the stratum corneum rigidifies it and thus makes it an excellent model to study the effect of the products being investigated in the field of improving the elasticity of the stratum corneum. The measurements are carried out 20 hours after the treatment.

The results are expressed in average percentage of variation of the elasticity modulus between the values, after application and before application, of the elasticity of the delipidated stratum corneum.

The results obtained with the product of Example 2 (called compound 5) and various known comparison products, of close formulation, are presented in the annexed FIG. 1.

On the figure:
Compound 1 is N-oleoyl (D,L)-serine;
Compound 2 is N-2-ethylhexanoyl (D,L)-serine;
Compound 3 is N-dodecanoyl (D,L)-serine;
Compound 4 is N-hexadecanoyl (D,L)-serine;
Compound 5 is N-2-ethylhexyloxycarbonyl (D,L)-serine;
Compound 6 is N-dodecyloxycarbonyl glycine;
Compound 7 is N-linoleoyl (D,L)-serine; and
Compound 8 is N-octanoyl (D,L)-serine.

Examples of Cosmetic Compositions [In these examples, the products designated by commercial trade names are the following:

KLUCEL H: hydroxypropylcellulose, sold by Hercules;

TWEEN 60: Sorbitan monostearate polyoxyethylenated with 20 moles of ethylene oxide, sold by ICI Americas; and CARBOPOL 940: Acrylic polymer crosslinked with a polyfunctional agent, sold by Goodrich.

EXAMPLE A

Gels

By admixing the following ingredients, three compositions in gel for having the following formulations have been prepared:

| (a) | |
|---|---|
| N-2-ethylhexyloxycarbonyl (D,L)-serine | 3 g |
| KLUCEL H | 1 g |
| Isopropanol | 48 g |
| Water | 48 g |
| (b) | |
| N-hexadecyloxycarbonyl (D,L)-serine | 3 g |
| KLUCEL H | 1 g |
| Isopropanol | 75 g |
| Water | 21 g |
| (c) | |
| Triethanolamine salt of N-2-ethylhexyloxycarbonyl (D,L)-serine | 2 g |
| KLUCEL H | 1 g |
| Ethanol | 49 g |
| Water | 48 g |

Analogous compositions are obtained by replacing the serine derivative with a corresponding derivative of threonine or citrulline.

EXAMPLE B

Lotions

Two lotions having the following formulations are prepared:

| (a) | |
|---|---|
| N-2-ethylhexyloxycarbonyl (D,L)-serine | 3 g |
| Isopropanol | 49 g |
| Water | 48 g |
| (b) | |
| Triethanolamine salt of N-hexadecyloxycarbonyl (D,L)-serine | 2 g |
| Isopropanol | 50 g |
| Water | 48 g |

Analogous compositions are obtained by replacing the serine derivative with the corresponding derivatives of threonine or citrulline.

EXAMPLE C

Cream for the Care of the Skin

A cream having the following composition is prepared:

| | |
|---|---|
| N-hexadecyloxycarbonyl (D,L)-serine | 3 g |
| Glycerol stearate | 2 g |
| TWEEN 60 | 1 g |
| Cetyl alcohol | 0.5 g |
| Stearic acid | 1.4 g |
| Triethanolamine | 0.7 g |
| CARBOPOL 940 (neutralized by triethanolamine) | 0.4 g |
| Liquid fraction of karite fat | 12 g |
| Synthesized perhydrosqualene | 12 g |
| Anti-oxidant | 0.05 g |
| Perfume | 0.5 g |
| Preservative | 0.3 g |
| Water, sufficient amount for | 100 g |

The anti-oxidant is a mixture of butylhydroxytoluene and butylhydroxyanisole.

The preservative is a mixture of the p-hydroxy benzoates of methyl, ethyl, propyl, butyl and isobutyl.

This cream (an oil-in-water emulsion) is prepared in the following manner:

CARBOPOL 940, neutralized by the triethanolamine, is added to one part of water (85 to 90%) and the mixture is heated to 75°–80° C. There is then added, with stirring, the fatty phase (glycerol stearate, TWEEN 60, stearic acid, cetyl alcohol, liquid fraction of karite fat, perhydrosqualene and anti-oxidant) heated to the same temperature. The triethanolamine is added last. After 10 minutes of stirring the serine derivative and the preservative, dissolved in the remainder of the water, are added. At the end of an additional 10 minutes the perfume is added. Then the stirring is stopped and the composition is cooled to ambient temperature (25° C.). Analogous compositions are obtained by replacing the serine derivative by the corresponding derivative of threonine or citrulline.

EXAMPLE D

Cream for the Care of the Skin

A cream having the following composition is prepared:

| | |
|---|---|
| N-2-ethylhexyloxycarbonyl (D,L)-serine | 4 g |
| Sorbitan monoisostearate | 5 g |
| Microcrystalline wax | 1 g |
| Petrolatum oil | 15 g |
| Corn germ oil | 4 g |
| Mixture of esters of $C_8$-$C_{10}$ fatty acids and $C_{12}$-$C_{18}$ fatty alcohols, sold by Henkel under the trade name "CETIOL-LC DEO" | 1 g |
| Gel of modified montmorillonite and neutral oil (triglycerides of caprylic and capric acids), sold by Dynamit Nobel under the trade name "MIGLYOL-GEL" | 5 g |
| Propylene glycol | 3 g |
| Anti-oxidant | 0.1 g |
| Preservative | 0.3 g |
| Water, sufficient amount for | 100 g |

This cream (water-in-oil emulsion) is prepared in a manner analogous to that described in Example C.

The anti-oxidant and preservative are the same as in Example C.

An analogous composition is obtained by replacing the serine derivative by the corresponding derivative of threonine or citrulline.

EXAMPLE E

Body Milk

A milk (fluid emulsion) having the following composition is prepared:

| | |
|---|---|
| Triethanolamine salt of N-hexadecyl-oxycarbonyl (D,L)-serine | 5 g |
| Glycerol stearate | 2 g |
| TWEEN 60 | 1 g |
| Stearic acid | 1.4 g |
| Triethanolamine | 0.7 g |
| CARBOPOL 940 (neutralized by triethanolamine | 0.2 g |
| Sweet almond oil | 3 g |
| Petrolatum oil | 8 g |
| Anti-oxidant | 0.05 g |
| Preservative | 0.3 g |
| Water, sufficient amount for | 100 g |

This body milk is prepared in a manner analogous to that described in Example C.

An analogous composition is obtained by replacing the serine derivative with the corresponding derivative of threonine or citrulline.

What is claimed is:

1. A topical cosmetic or pharmaceutical composition comprising, as an active ingredient, at least one urethane derivative in a vehicle compatible for application to the skin or hair or both, wherein said urethane derivative is selected from the group consisting of (i) a compound having the formula $$R'O-CO-NH-CH(R)-COOH \quad (I)$$

wherein

R represents $-CH_2OH$, $-CHOH-CH_3$ or $-(CH_2)_3-NH-CO-NHY$,

Y represents $-H$ or $-COOR'$,

R' represents linear or branched alkyl, optionally unsaturated, having 8-24 carbon atoms, or a monocyclic cycloalkyl substituted by an alkyl whose total number of carbon atoms is equal to or greater than 10;

(ii) a salt of the compound of formula I selected from the group consisting of those salts which are compatible with application to the skin;

(iii) a mixture of the compounds of formula I;

(iv) a mixture of the compounds of formula I and salts thereof compatible with application to the skin; and (v) a mixture of the salts, compatible with application to the skin, of the compounds of formula I;

wherein said salt compatible with application to the skin is selected from the group consisting of a sodium salt, a zinc salt, a magnesium salt, an aluminum salt, a cupric salt and a quaternary ammonium salt of a cation having the formula $$R^2-\overset{R^1}{\underset{R^3}{N+}}-R^4$$

wherein $R^1$, $R^2$, $R^3$ and $R^4$, each independently, represent $-CH_3$, $-CH_2-C_6H_5$ or $-CH_2-CH_2OH$; and said urethane derivative being present in an amount ranging from 0.1 to 15 weight percent based on the total weight of said composition.

2. The composition of claim 1 wherein said urethane derivative is present in an amount ranging from 0.5 to 5 weight percent based on the total weight of said composition.

3. A cosmetic treatment process for improving the appearance and elasticity of the skin of a person having dry skin or for preventing the appearance of aesthetic disorders caused by dry skin, said process comprising applying to the skin of the parts of the body affected or optionally to the scalp, effective amount of the composition of claim 1 sufficient to effect improvement in appearance and elasticity of skin thus treated; and preventing the appearance of aesthetic skin disorders.

* * * * *